United States Patent [19]

Schölkens

[11] Patent Number: 5,231,080
[45] Date of Patent: Jul. 27, 1993

[54] METHOD FOR THE TREATMENT OF ATHEROSCLEROSIS, THROMBOSIS, AND PERIPHERAL VESSEL DISEASE

[75] Inventor: Bernward Schölkens, Kelkheim (Taunus), Fed. Rep. of Germany

[73] Assignee: Hoechst Aktiengesellschaft, Frankfurt am Main, Fed. Rep. of Germany

[21] Appl. No.: 678,187

[22] Filed: Mar. 29, 1991

Related U.S. Application Data

[63] Continuation of Ser. No. 393,058, Aug. 11, 1989, abandoned, which is a continuation of Ser. No. 917,430, Oct. 10, 1986, abandoned.

[30] Foreign Application Priority Data

Oct. 15, 1985 [DE] Fed. Rep. of Germany ....... 3536687

[51] Int. Cl.$^5$ .............................................. A61K 37/00
[52] U.S. Cl. ............................................................ 514/2
[58] Field of Search ............................................ 514/2

[56] References Cited

U.S. PATENT DOCUMENTS

| 4,350,704 | 9/1982 | Hoefle et al. | 514/412 |
| 4,374,829 | 2/1983 | Harris et al. | 530/800 |
| 4,374,847 | 2/1983 | Gruenfeld | 514/411 |

(List continued on next page.)

FOREIGN PATENT DOCUMENTS

| 0088341 | of 0000 | European Pat. Off. . |
| 0012845 | 7/1980 | European Pat. Off. . |
| 0018549 | 11/1980 | European Pat. Off. . |
| 0037231A2 | 10/1981 | European Pat. Off. . |
| 0046953 | 3/1982 | European Pat. Off. . |
| 0048159 | 3/1982 | European Pat. Off. . |
| 0049658 | 4/1982 | European Pat. Off. . |
| 0050850A1 | 5/1982 | European Pat. Off. . |
| 0079521 | 5/1982 | European Pat. Off. . |
| 0052991 | 6/1982 | European Pat. Off. . |
| 0090362 | 10/1982 | European Pat. Off. . |
| 0012401 | 5/1983 | European Pat. Off. . |
| 0080822 | 6/1983 | European Pat. Off. . |
| 0115091 | 8/1984 | European Pat. Off. . |
| 0196841 | 10/1986 | European Pat. Off. . |
| 3143946 | of 0000 | Fed. Rep. of Germany . |
| 3322530 | 1/1985 | Fed. Rep. of Germany . |
| 813034 | 4/1981 | Finland . |
| 812859 | 3/1982 | Finland . |
| 813283 | 4/1982 | Finland . |
| 813422 | 5/1982 | Finland . |
| 2491469 | 4/1982 | France . |
| 64085 | 4/1981 | Israel . |
| 57-77672 | 5/1982 | Japan . |
| 57-112359 | 7/1982 | Japan . |
| 57-91974 | 8/1982 | Japan . |
| 198535 | 9/1984 | New Zealand . |
| 198702 | 8/1985 | New Zealand . |
| 81/5988 | 8/1982 | South Africa . |
| 83/2229 | 12/1983 | South Africa . |
| 2086390 | 5/1982 | United Kingdom . |
| 2095682 | 10/1982 | United Kingdom . |

OTHER PUBLICATIONS

Leonard et al., J. Am. Chem. Soc., 78, 3463 (1956).
Leonard et al., J. Am. Chem. Soc., 81, 5627 (1959).

(List continued on next page.)

*Primary Examiner*—S. J. Friedman
*Attorney, Agent, or Firm*—Finnegan, Henderson, Farabow, Garrett & Dunner

[57] ABSTRACT

The invention relates to a method for the treatment of atherosclerosis, thrombosis and/or of peripheral vessel disease by administration of angiotensin converting enzyme inhibitors. Administration of compounds of the formula I $$R^3OOC-\underset{R^4}{CH}-\underset{R^5}{N}-\underset{O}{\overset{\|}{C}}-\underset{R^1}{CH}-NH-\underset{COOR^2}{CH}-(CH_2)_n-R \quad (I)$$

in which n is 1 or 2, R, $R^1$, $R^2$ and $R^3$ are identical or different and each denotes hydrogen or an organic radical, and $R^4$ and $R^5$ form, together with the atoms carrying them, a mono-, bi- or tricyclic heterocyclic ring system, is preferred. The invention also relates to angiotensin converting enzyme inhibitors and to agents containing them for administration for the treatment of the abovementioned diseases.

6 Claims, No Drawings

U.S. PATENT DOCUMENTS

| | | | |
|---|---|---|---|
| 4,425,355 | 1/1984 | Hoefle et al. | 514/412 |
| 4,442,089 | 4/1984 | Horovitz | 514/19 |
| 4,515,803 | 5/1985 | Henning et al. | 514/19 |
| 4,525,301 | 6/1985 | Henning et al. | 548/411 |
| 4,558,037 | 12/1985 | Chan et al. | |
| 4,558,064 | 12/1985 | Teetz et al. | 514/412 |
| 4,558,065 | 12/1985 | Urbach et al. | 514/412 |
| 4,584,285 | 4/1986 | Doll et al. | 514/412 |
| 4,591,598 | 5/1986 | Urbach et al. | 548/452 |
| 4,614,805 | 9/1986 | Urbach et al. | 514/412 |
| 4,620,012 | 10/1986 | Henning et al. | 514/411 |
| 4,624,962 | 11/1986 | Henning et al. | 548/411 |
| 4,659,838 | 4/1987 | Lerch | 514/412 |
| 4,663,307 | 5/1987 | Girard et al. | 514/336 |
| 4,668,796 | 5/1987 | Geiger et al. | 514/412 |
| 4,668,797 | 5/1987 | Urbach et al. | 548/452 |
| 4,678,800 | 7/1987 | Stanton et al. | 514/412 |
| 4,684,662 | 8/1987 | Henning et al. | 514/411 |
| 4,691,022 | 9/1987 | Henning et al. | 514/411 |
| 4,714,708 | 12/1987 | Urbach et al. | 514/412 |
| 4,727,160 | 2/1988 | Teetz et al. | 545/41 |
| 4,808,573 | 2/1989 | Gold et al. | 548/492 |
| 4,822,894 | 4/1989 | Geiger et al. | 514/411 |
| 4,831,157 | 5/1989 | Gold et al. | 548/492 |
| 4,849,524 | 7/1989 | Henning et al. | 548/411 |
| 4,868,307 | 9/1989 | Barton et al. | 514/412 |
| 4,886,827 | 12/1989 | Urbach et al. | 514/412 |
| 4,920,144 | 4/1990 | Urbach et al. | 514/412 |
| 4,983,623 | 1/1991 | Henning et al. | 514/411 |
| 4,997,260 | 12/1991 | Henning et al. | 514/411 |

OTHER PUBLICATIONS

Koelsch et al., J. Org. Chem., 26, 1104 (1961).
Griot et al., Helv. Chim. Acta, 42, 121 (1959).
Bonnett et al., J. Chem. Soc., 2087 (1959).
Battersby et al., J. Chem. Soc., 4333 (1958).
Rosenblatt et al., The Chemistry Of Functional Groups. Supplement F: The Chemistry of Amino, Nitroso and Nitro Compounds And Their Derivatives. Part II, S. Patai, ed., Wiley & Sons: New York 1982, pp. 1100–1104.
L. W. Haynes, Enamines, A. G. Cook, ed., Marcel Decker, Inc.: 1969, pp. 68–79, 261–269, 413.
Fieser & Fieser, Reagents For Organic Synthesis, vol. 1, pp. 644–651 (1967).
Boehme et al., Iminium Salts in Organic Chemistry, Part I (E. C. Taylor, ed.), Wiley & Sons: New York, 1976, p. 143.
S. Dayagi et al., The Chemistry Of Functional Groups. The Chemistry Of The Carbon-Nitrogen Double Bond, S. Patai, ed., Wiley & Sons: New York, 1970, p. 119.
W. Greenlee et al., J. Med. Chem., 28, 434–442 (1985).
K. Ogawa et al., J. Chem. Soc., Perkin Trans. I, 3031–3035 (1982).
R. Bacon and D. Stewart, J. Chem. Soc. (C), 1384–1387 (1966).
R. Bacon et al., J. Chem. Soc. (C), 1388–1389 (1966).
Patchett et al., Nature, 288, 280–283 (1980).
Booth et al., Chemistry and Industry, 466–467 (1956).
Booth et al., J. Chem. Soc., Part I, 1050–1054 (1959).
Murakoshi et al., Chemical Abstracts, 61, 9465(e) (1964).
Cushman et al., Fed. Proc., 38 (13), 2778–2782 (1979).
Houben-Weyl, Methoden der Organischen Chemie, 7(2b), 1403–1404 (1976).
Katritskaya, Dzh. Lagorskaya Khimia Geterosikl. Soedin., Moskow 1963, pp. 155–158.
Anderson, Jr. et al., J. Org. Chem., 43(1), 54–57 (1978).
Bertho et al., Synthesen In Der 2-Azabicyclo[0.3.3]-octan-Reihe, Chemische Berichte, 92(7), 2218–2235 (1959).
Farkas et al., J. Org. Chem., 22, 1261–1263 (1957).
Taylor et al., J. Org. Chem., 38(16), 2817–2821 (1973).
Taylor et al., Heterocycles, 25, 343–345 (1987).
English language translation of Mitzlaff et al., Liebig's Ann. Chem., 1713–1733 (1978).
Quarterly Reviews 25: 323–341 (1971).
Chem. Berichte 86: 1524–1528 (1953).
Chem. Abst. 49/1955/3009c.
Xiang et al. Chem Abstracts, CA (100):150853c (1984), p. 3.
B. A. Schoelkens et al., "Programm/Abstracts", p. 20.
M. Catalano et al., Angiology—Journal of Vascular Diseases, vol. 36, No. 5, May 1985, 293–296.
Noriyuki Someya et al., Journal of Cardiovascular Pharmacology, vol. 6, No. 5, 1984, 840–843.
G. Trubestein et al., DTSCH. MED. WOCHENSCHR., vol. 109, No. 22, 1984, 857–860.
Sakae Wasa et al., Atherosclerosis, vol. 40, 1981, 263–271.
Seiji Miyazaka et al., British Med. Journal, vol. 284, No. 6312, Jan., 1982, 310–311.
Kiyoshi Yamagami et al., Folia Opthalmol. Jpn., vol. 34, No. 2, 1983, 290–297.

METHOD FOR THE TREATMENT OF ATHEROSCLEROSIS, THROMBOSIS, AND PERIPHERAL VESSEL DISEASE

This application is a continuation of application Ser. No. 07/393,058 filed Aug. 11, 1989, which is a continuation of application Ser. No. 06/917,430 filed Oct. 10, 1986 both now abandoned.

The invention relates to a method for the treatment of atherosclerosis, of thrombosis and/or of peripheral vessel disease by oral or parenteral administration of compounds which inhibit angiotensin converting enzyme. Particularly suitable for this purpose are compounds of the formula I

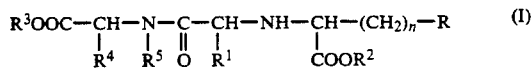

in which n is 1 or 2,

R = hydrogen, an optionally substituted aliphatic radical having 1–8 carbon atoms, an optionally substituted alicyclic radical having 3–9 carbon atoms, an optionally substituted aromatic radical having 6–12 carbon atoms, an optionally substituted araliphatic radical having 7–14 carbon atoms, an optionally substituted alicyclic-aliphatic radical having 7–14 carbon atoms, or a radical $OR^a$ or $SR^a$, in which $R^a$ represents an optionally substituted aliphatic radical having 1–4 carbon atoms, an optionally substituted aromatic radical having 6–12 carbon atoms, or an optionally substituted heteroaromatic radical having 5–12 ring atoms, $R^1$ denotes hydrogen, an optionally substituted aliphatic radical having 1–6 carbon atoms, an optionally substituted alicyclic radical having 3–9 carbon atoms, an optionally substituted alicyclicaliphatic radical having 4–13 carbon atoms, an optionally substituted aromatic radical having 6–12 carbon atoms, an optionally substituted araliphatic radical having 7–16 carbon atoms, an optionally substituted heteroaromatic radical having 5–12 ring atoms, or the side chain, protected where necessary, of a naturally occurring α-amino acid, $R^2$ and $R^3$ are identical or different and denote hydrogen, an optionally substituted aliphatic radical having 1–6 carbon atoms, an optionally substituted alicyclic radical having 3–9 carbon atoms, an optionally substituted aromatic radical having 6–12 carbon atoms, or an optionally substituted araliphatic radical having 7–16 carbon atoms, and $R^4$ and $R^5$ form, together with the atoms carrying them, a heterocyclic, mono-, bi- or tricyclic ring system having 4 to 15 carbon atoms.

Particularly suitable ring systems of this type are those of the following group:

Tetrahydroisoquinoline (A); decahydroisoquinoline (B); octahydroindole (C); octahydrocyclopenta[b]pyrrole (D); 2-azaspiro[4.5]decane (E); 2-azaspiro[4.4]nonane (F); spiro[(bicyclo[2.2.1]heptane)-2,3'-pyrrolidine](G); spiro[(bicyclo[2.2.2]octane)-2,3'-pyrrolidine](H); 2-azatricyclo[4.3.0. 9]decane (I); decahydrocyclohepta[b]pyrrole (J); octahydroisoindole (K); octahydrocyclopenta[c]pyrrole (L); 2,3,3a,4,5,7a-hexahydroindole (M); 2-azabicyclo[3.1.0]hexane (N); all of which can optionally be substituted. However, the unsubstituted systems are preferred.

In the case of compounds which have several chiral atoms, all possible diastereomers are suitable, as racemates or enantiomers or mixtures of various diastereomers.

The cyclic amino acid esters which are suitable have the following structural formulae.

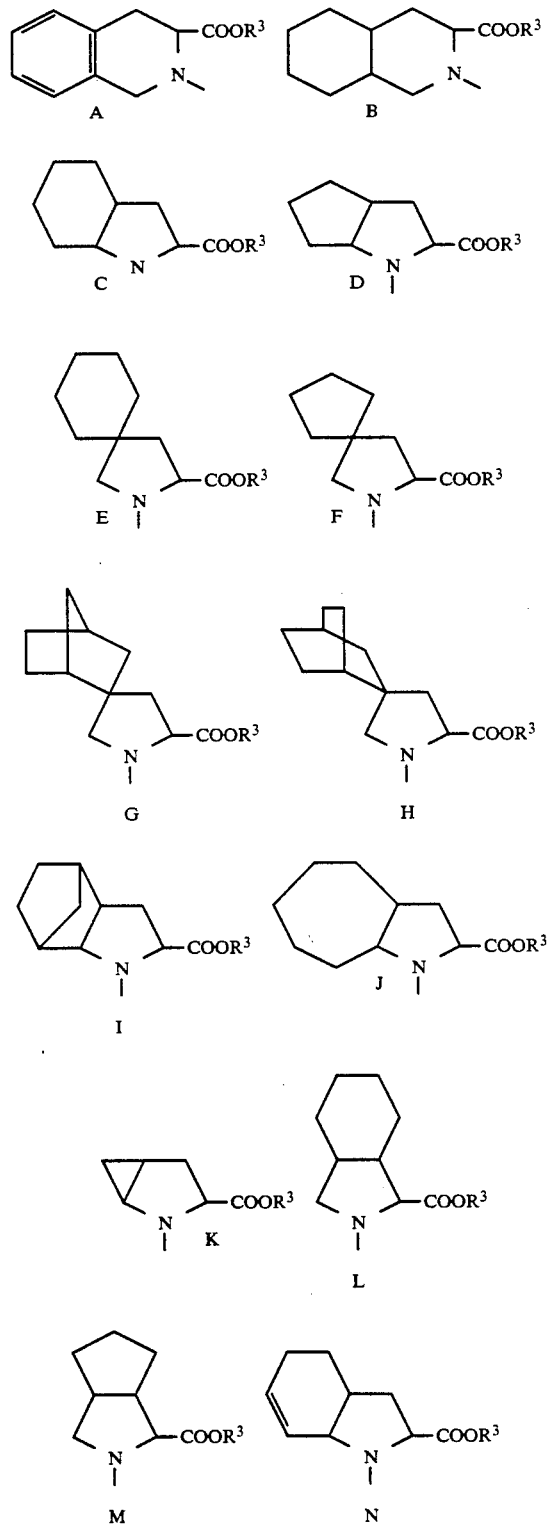

A preferred embodiment comprises use of compounds of the formula I in which n is 1 or 2, R denotes hydrogen, alkyl having 1-8 carbon atoms, alkenyl having 2-6 carbon atoms, cycloalkyl having 3-9 carbon atoms, aryl which has 6-12 carbon atoms and can be mono-, di- or trisubstituted by ($C_1$-$CH_4$)-alkyl, ($C_1$-$C_4$)-alkoxy, hydroxyl, halogen, nitro, amino, aminomethyl, ($C_1$-$C_4$)-alkylamino, di-($C_1$-$C_4$)-alkylamino, ($C_1$-$C_4$)-alkanoylamino, methylenedioxy, carboxyl, cyano and/or sulfamoyl, alkoxy having 1-4 carbon atoms, aryloxy which has 6-12 carbon atoms and can be substituted as described above for aryl, mono- or bicyclic heteroaryloxy which has 5-7 or 8-10 ring atoms respectively, 1 to 2 of these ring atoms representing sulfur or oxygen atoms and/or 1 to 4 of these ring atoms representing nitrogen, and which can be substituted as described above for aryl, amino-($C_1$-$C_4$)-alkyl, ($C_1$-$C_4$)-alkanoylamino-($C_1$-$C_4$)-alkyl, ($C_7$-$C_{13}$)-aroylamino-($C_1$-$C_4$)-alkyl, ($C_1$-$C_4$)-alkoxycarbonylamino-($C_1$-$C_4$)-alkyl, ($C_6$-$C_{12}$)-aryl-($C_1$-$C_4$)-alkoxycarbonylamino-($C_1$-$C_4$)-alkyl, ($C_6$-$C_{12}$)-aryl-($C_1$-$C_4$)-alkylamino-($C_1$-$C_4$)-alkyl, ($C_1$-$C_4$)-alkylamino-($C_1$-$C_4$)-alkyl, di-($C_1$-$C_4$)-alkylamino-($C_1$-$C_4$)-alkyl, guanidino-($C_1$-$C_4$)-alkyl imidazolyl, indolyl, ($C_1$-$C_4$)-alkylthio, ($C_1$-$C_4$)-alkylthio-($C_1$-$C_4$)-alkyl, ($C_6$-$C_{12}$)-arylthio-($C_1$-$C_4$)-alkyl which can be substituted in the aryl moiety as described above for aryl, ($C_6$-$C_{12}$)-aryl-($C_1C_4$)-alkylthio which can be substituted in the aryl moiety as described above for aryl, carboxy-($C_1$-$C_4$)-alkyl, carboxyl, carbamoyl, carbamoyl-($C_1$-$C_4$)-alkyl, ($C_1$-$C_4$)-alkoxycarbonyl-($C_1$-$C_4$)-alkyl, ($C_6$-$C_{12}$)-aryloxy-($C_1$-$C_4$)-alkyl which can be substituted in the aryl moiety as described above for aryl, or ($C_6$-$C_{12}$)-aryl-($C_1$-$C_4$)-alkoxy which can be substituted in the aryl moiety as described above for aryl, $R^1$ denotes hydrogen, alkyl having 1-6 carbon atoms, alkenyl having 2-6 carbon atoms, alkynyl having 2-6 carbon atoms, cycloalkyl having 3-9 carbon atoms cycloalkenyl having 5-9 carbon atoms, ($C_3$-$C_9$)-cycloalkyl-($C_1$-$C_4$)-alkyl, ($C_5$-$C_9$)-cycloalkenyl($C_1$-$C_4$)-alkyl, optionally partially hydrogenated aryl which has 6-12 carbon atoms and can be substituted as described above for R, ($C_6$-$C_{12}$)-aryl-($C_1$-$C_4$)-alkyl or ($C_7$-$C_{13}$)-aroyl-($C_1$ or $C_2$)-alkyl, both of which can be substituted as the abovementioned aryl, mono- or bicyclic, optionally partially hydrogenated heteroaryl which has 5-7 or 8-10 ring atoms respectively, 1 or 2 of these ring atoms representing sulfur or oxygen atoms and/or 1 to 4 of these ring atoms representing nitrogen atoms, and which can be substituted as the abovementioned aryl, or the optionally protected side chain of a naturally occurring α-amino acid $R^1$-CH($NH_2$)—COOH, $R^2$ and $R^3$ are identical or different and denote hydrogen, alkyl having 1-6 carbon atoms, alkenyl having 2-6 carbon atoms, di-($C_1$-$C_4$)-alkylamino-($C_1$-$C_4$)-alkyl, ($C_1$-$C_5$)-alkanoyloxy-($C_1$-$C_4$)-alkyl, ($C_1$-$C_6$)-alkoxycarbonyloxy-($C_1$-$C_4$)-alkyl, ($C_7$-$C_{13}$)-aroyloxy-($C_1$-$C_4$)-alkyl, ($C_6$-$C_{12}$)-aryloxycarbonyloxy-($C_1$-$C_4$)-alkyl, aryl having 6-12 carbon atoms, ($C_6$-$C_{12}$)-aryl-($C_1$-$C_4$)-alkyl, ($C_3$-$C_9$)-cycloalkyl or ($C_3$-$C_9$)-cycloalkyl-($C_1$-$C_4$)-alkyl, and $R^4$ and $R^5$ have the abovementioned meaning.

A particularly preferred embodiment comprises use of compounds of the formula I in which n is 1 or 2, R denotes ($C_1$-$C_6$)-alkyl, ($C_2$-$C_6$)-alkenyl, ($C_3$-$C_9$)-cycloalkyl, amino-($C_1$-$C_4$)-alkyl, ($C_2$-$C_5$)-acylamino-($C_1$-$C_4$)-alkyl, ($C_7$-$C_{13}$)-aroylamino-($C_1$-$C_4$)-alkyl, ($C_1$-$C_4$)-alkoxycarbonylamino-($C_1$-$C_4$)-alkyl, ($C_6$-$C_{12}$) aryl-($C_1$-$C_4$)-alkoxycarbonylamino-($C_1$-$C_4$)-alkyl, ($C_6$-$C_{12}$)-aryl which can be mono-, di- or trisubstituted by ($C_1$-$C_4$)-alkyl, ($C_1$-$C_4$)-alkoxy, hydroxyl, halogen, nitro, amino, ($C_1$-$C_4$)-alkylamino, di-($C_1$-$C_4$)-alkylamino and/or methylenedioxy, or 3-indolyl, in particular methyl, ethyl, cyclohexyl, tert.-butoxycarbonylamino-($C_1$-$C_4$)-alkyl, benzoyloxycarbonylamino-($C_1$-$C_4$)-alkyl, or phenyl which can be mono- or disubstituted, or in the case of methoxy tri-substituted, by phenyl, ($C_1$-$C_2$)-alkyl, ($C_1$ or $C_2$)alkoxy, hydroxyl, fluorine, chlorine, bromine, amino, ($C_1$-$C_4$)-alkylamino, di-($C_1$-$C_4$)-alkylamino, nitro and/or methylenedioxy, $R^1$ denotes hydrogen or ($C_1$-$C_6$)-alkyl which can optionally be substituted by amino, ($C_1$-$C_6$)-acylamino or benzoylamino, ($C_2$-$C_6$)-alkenyl, ($C_3$-$C_9$)-cycloalkyl, ($C_5$-$C_9$)-cycloalkenyl, ($C_3$-$C_7$)-cycloalkyl-($C_1$-$C_4$)-alkyl, ($C_6$-$C_{12}$)-aryl or partially hydrogenated aryl, each of which can be substituted by ($C_1$-$C_4$)-alkyl, ($C_1$ or $C_2$)-alkoxy or halogen, ($C_6$-$C_{12}$)-aryl-($C_1$ to $C_4$)-alkyl or ($C_7$-$C_{13}$)-aroyl-($C_1$-$C_2$)-alkyl, both of which can be substituted in the aryl radical as defined above, a mono- or bicyclic heterocyclic radical having 5 to 7 or 8 to 10 ring atoms respectively, 1 to 2 of these ring atoms representing sulfur or oxygen atoms and/or 1 to 4 of these ring atoms representing nitrogen atoms, or a side chain of a naturally occurring, optionally protected α-amino acid, but in particular hydrogen, ($C_1$-$C_3$)-alkyl, ($C_2$ or $C_3$)-alkenyl, the optionally protected side chain or lysine, benzyl, 4-methoxybenzyl, 4-ethoxybenzyl, phenethyl, 4-aminobutyl or benzoylmethyl, $R^2$ and $R^3$ denote identical or different radicals hydrogen, ($C_1$-$C_6$)-alkyl, ($C_2$-$C_6$)-alkenyl or ($C_6$-$C_{12}$)-aryl-($C_1$-$C_4$)-alkyl, but in particular hydrogen, ($C_1$-$C_4$)-alkyl or benzyl, and $R^4$ and $R^5$ have the abovementioned meaning.

It is particularly preferred to use compounds of the formula I in which n is 2,

R denotes phenyl, $R^1$ denotes methyl, $R^2$ and $R^3$ denote identical or different ($C_1$-$C_6$)-alkyl radicals or ($C_7$-$C_{10}$)-aralkyl radicals such as benzyl or nitrobenzyl, and $R^4$ and $R^5$ together represent a radical of the formula

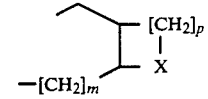

in which m denotes 0 or 1, p denotes 0, 1 or 2, and

X denotes —$CH_2$—, —$CH_2$-$CH_2$— or —CH=CH—, it also being possible for a 6 ring formed with X to be benzene ring.

In this context and in the following, aryl is to be understood preferably to be substituted phenyl, biphenylyl or naphthyl. A corresponding statement applies to radicals derived from aryl, such as aryloxy and arylthio. Aroyl is particularly understood to be benzoyl. Aliphatic radicals can be straight-chain or branched.

A mono- or bicyclic heterocyclic radical having 5 to 7 or 8 to 10 ring atoms respectively, 1 to 2 of these ring atoms representing sulfur or oxygen atoms and/or 1 to 4 of these ring atoms representing nitrogen atoms, is to be understood to be, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, cinnolinyl, pteridinyl, oxazolyl, isoxazolyl, thiazolyl or isothiazolyl. These radicals can also be partially or completely hydrogenated.

Naturally occurring α-amino acids are described in, for example, Houben-Weyl, Methoden der Organischen Chemie (Methods of Organic Chemistry), Vols. XV/1 and VX/2.

Where $R^1$ represents a side chain of a protected naturally occurring α-amino acid such as, for example, protected Ser, Thr, Asp, Asn, Glu, Gln, Arg, Lys, Hyl, Cys, Orn, Cit, Tyr, Trp, His or Hyp, the preferred protective groups are the groups customary in peptide chemistry (cf. Houben-Weyl, Vols. XV/1 and XV/2). In the case where $R^1$ denotes the protected side chain of lysine, the known amino protective groups, but in particular Z, Boc or (C$_1$-C$_6$)-alkanoyl, are preferred. Suitable and preferred as O-protective groups for tyrosine are (C$_1$-C$_6$)-alkyl, in particular methyl or ethyl.

ACE inhibitors of the formula I can be prepared by reacting together their fragments in a suitable solvent, where appropriate in the presence of a base and/or of a coupling auxiliary, where appropriate reduction of unsaturated compounds which have resulted as intermediates, such as Schiff's bases, and elimination of protective groups which have been introduced temporarily to protect reactive groups and, where appropriate, conversion of the resulting compounds into their physiologically tolerated salts.

It is possible in the said manner to react compounds of the formula V with compounds of the formula VI $$R^3OOC-CH-N-H \atop R^4 \quad R^5 \qquad (V)$$

$$HOOC-CH-NH-CH-(CH_2)_n-R \atop R^1 \qquad COOR^2 \qquad (VI)$$

The reaction of these compounds can, for example, be carried out in analogy to known peptide coupling processes in the presence of coupling auxiliaries such as carbodiimides (for example dicyclohexylcarbodiimide), diphenylphosphoryl azide, alkanephosphoric anhydrides, dialkylphosphinic anhydrides or N,N-succinimidyl carbonates in CH$_3$CN. Amino groups in compounds of the formula V can be activated with tetraethyl diphosphite. The compounds of the formula VI can be converted into active esters for example with 1-hydroxybenzotriazole), mixed anhydrides (for example with chloroformic esters), azides or carbodiimide derivatives, and thus be activated (cf. Schröder, Lübke, The Peptides, Vol. 1, New York, 1965, pages 76-136).

It is likewise possible to react compounds of the formula VII with compounds of the formula VIII, with the formation of compounds of the formula I

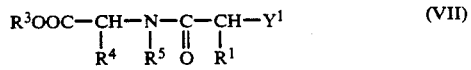

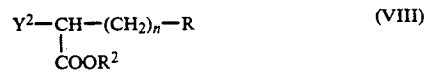

in which either $Y^1$ represents amino and $Y^2$ represents a leaving group, or $Y^1$ represents a leaving group and $Y^2$ represents amino. Examples of suitable leaving groups are Cl, Br, I, alkylsulfonyloxy or arylsulfonyloxy.

Alkylations of this type are advantageously carried out in water or an organic solvent, in the presence of a base.

Furthermore, compounds of the formula IX can be condensed with compounds of the formula X

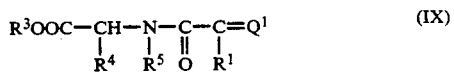

in which either $Q^1$ represents amino+hydrogen and $Q^2$ represents oxo, or $Q^1$ represents oxo and $Q^2$ represents amino+hydrogen.

The condensation is advantageously carried out in water or an organic solvent such as a lower alcohol, and in the presence of a reducing agent such as NaBH$_3$CN, whereupon compounds of the formula I are obtained directly. However, it is also possible to reduce the Schiff's bases or enamines which result as intermediates, where appropriate after previous isolation, with the formation of compounds of the formula I, for example by hydrogenation in the presence of a transition metal catalyst.

Finally, reaction of compounds of the formula IX ($Q^1$=H+NH$_2$) with compounds of the formula XI, or their reaction with compounds of the formulae XII and XIII, also results in compounds of the formula I (n=2), $$R^2OOC-CH=CH-CO-R \qquad (XI)$$

$$OCH-COOR^2 \qquad (XII)$$

$$R-CO-CH_3 \qquad (XIII)$$

there being reduction of Schiff's bases produced as intermediates, and conversion of a carbonyl group into methylene by reduction.

In the abovementioned formulae V-XIII, R-R$^5$ and n are as defined in formula I. Protective groups introduced temporarily to protect reactive groups not involved in the reaction are eliminated after reaction is complete in a manner known per se (cf. Schröder, Lübke, loc. cit., pages 1-75 and 246-270).

It is possible and particularly advantageous to use the following compounds in the method according to the invention: N-(1-S-carboethoxy-3-phenylpropyl)-S-alanyl-S-1,2,3,4-tetrahydroisoquinoline-3-carboxylic acid N-(1-S-carboethoxy-3-cyclohexylpropyl)-S-alanyl-S-1,2,3,4-tetrahydroisoquinoline-3-carboxylic acid N-(1-S-carboethoxy-3-phenylpropyl)-S-lysyl-S-1,2,3,4-tetrahydroisoquinoline-3-carboxylic acid N-(1-S-carboethoxy-3-phenylpropyl)-O-ethyl-S-tyrosyl-S-1,2,3,4-tetrahydroisoquinoline-3-carboxylic acid N-(1-S-carboethoxy-3-phenylpropyl)-S-alanyl-3S-decahydro-isoquinoline-3-carboxylic acid N-(1-S-carboethoxy-3-phenylpropyl)-S-alanyl-(2S,3aS,7aS)-octahydroindole-2-carboxylic acid N-(1-S-carboethoxy-3-cyclohexylpropyl)-S-alanyl-(2S,3aS,7aS)-octahydroindole-2-carboxylic acid N-(1-S-carboethoxy-3-phenylpropyl)-S-lysyl-(2S,3aS,7aS)-octahydroindole-2-carboxylic acid N-(1-S-carboethoxy-3-cyclohexylpropyl)-S-lysyl-(2S,3aS,7aS)-octahydroindole-2-carboxylic acid N-(1-S-carboethoxy-3-cyclohexylpropyl)-S-lysyl-(2S,3aS,7aS)-octahydroindole-2-carboxylic acid N-(1-S-carboethoxy-3-phenylpropyl)-O-methyl-S-tyrosyl-(2S,3aS,7aS)-octahydroindole-2-carboxylic acid N-(1-S-carboethoxy-3-phenylpropyl)-O-ethyl-S-tyrosyl-(2S,3aS,7aS)-octahydroindole-2-carboxylic acid N-(1-S-carboethoxy-3-(3,4-dimethylphenylpropyl)-S-alanyl-(2S,3aS,7aS)-octahydroindole-2-carboxylic acid N-[1-S-carboethoxy-3-(4-fluorophenyl)-propyl]-S-alanyl-(2S,3aS,7aS)-octahydroindole-2-carboxylic acid N-[1-S-carboethoxy-3-(4-methoxyphenyl)-propyl]-S-alanyl-(2S,3aS,7aS)-octahydroindole-2-carboxylic acid N-[1-S-carboethoxy-3-(3,4-dimethoxyphenyl)-propyl]-S-alanyl-(2S,3aS,7aS)-octahydroindole-2-carboxylic acid N-(1-S-carboethoxy-3-cyclopentylpropyl)-S-alanyl-(2S,3aS,7aS)-octahydroindole-2-carboxylic acid N-(1-S-carboethoxy-3-phenylpropyl)-S-alanyl-(2S,3aR,7aS)-octahydroindole-2-carboxylic acid N-(1-S-carboethoxy-3-cyclohexylpropyl)-S-alanyl-(2S,3aR,7aS)-octahydroindole-2-carboxylic acid N-(1-S-carboethoxy-3-phenylpropyl)-S-lysyl-(2S,3aR,7aS)-octahydroindole-2-carboxylic acid N-(1-S-carboethoxy-3-cyclohexylpropyl)-S-lysyl-(2S,3aR,7aS)-octahydroindole-2-carboxylic acid N-(1-S-carboethoxy-3-phenylpropyl)-O-ethyl-S-tyrosyl-(2S,3aS,7aR)-octahydroindole-2-carboxylic acid N-(1-S-carboethoxy-3-phenylpropyl)-S-alanyl-(2S,3aR,7aR)-octahydroindole-2-carboxylic acid N-(1-S-carboethoxy-3-phenylpropyl)-S-lysyl-(2S,3aR,7aS)-octahydroindole-2-carboxylic acid N-(1-S-carboethoxy-3-cyclohexylpropyl)-S-alanyl-(2S,3aR,7aR)-octahydroindole-2-carboxylic acid N-(1-S-carboethoxy-3-cyclohexylpropyl)-O-ethyl-S-tyrosyl-(2S,3aR,7aR)-octahydroindole-2-carboxylic acid N-(1-S-carboethoxy-3-phenylpropyl)-S-alanyl-(2S,3aS,7aR)-octahydroindole-2-carboxylic acid N-(1-S-carboethoxy-3-phenylpropyl)-O-ethyl-S-tyrosyl-(2S,3aS,7aS)-octahydroindole-2-carboxylic acid N-(1-S-carboethoxy-3,4-dimethylphenylpropyl)-S-alanyl-(2S,3aS,7aS)-octahydroindole-2-carboxylic acid N-[1-S-carboethoxy-3-(4-fluorophenyl)-propyl]-S-alanyl-(2S,3aS,7aS)-octahydroindole-2-carboxylic acid N-[1-S-carboethoxy-3-(4-methoxyphenyl)-propyl]-S-alanyl-(2S,3aS,7aS)-octahydroindole-2-carboxylic acid N-[1-S-carboethoxy-3-(3,4-dimethoxyphenyl)-propyl]-S-alanyl-(2S,3aS,7aS)-octahydroindole-2-carboxylic acid N-(1-S-carboethoxy-3-cyclopentylpropyl)-S-alanyl-(2S,3aS,7aS)-octahydroindole-2-carboxylic acid N-(1-S-carboethoxy-3-phenylpropyl)-S-alanyl-cis-endo-2-azabicyclo[3.3.0]octane-3-S-carboxylic acid N-(1-S-carboethoxy-3-phenylpropyl)-S-lysyl-cis-endo-2azabicyclo[3.3.0]octane-3-S-carboxylic acid N-(1-S-carboethoxy-3-cyclohexylpropyl)-S-alanyl-cis-endo-2-azabicyclo[3.3.0]octane-3-S-carboxylic acid N-(1-S-carboxy-3-cyclohexylpropyl)-S-alanyl-cis-endo-2azabicyclo[3.3.0]octane-3-S-carboxylic acid N-(1-S-carboethoxybutyl)-S-alanyl-cis-endo-2-azabicyclo[3.3.0]octane-3-S-carboxylic acid N-(1-S-carboethoxy-3-(3,4-dimethoxyphenylpropyl)-S-alanyl-cis-endo-2-azabicyclo[3.3.0]octane-3-S-carboxylic acid N-(1-S-carboethoxy-3-cyclopentylpropyl)-S-alanyl-cis-endo-azabicyclo-[3.3.0]octane-3-S-carboxylic acid N-(1-S-carboethoxy-3-phenylpropyl)-O-methyl-S-tyrosyl-cis-endo-2-azabicyclo[3.3.0]octane-3-S-carboxylic acid N-(1-S-carboethoxy-3-phenylpropyl)-O-ethyl-S-tyrosyl-cis-endo-2-azabicyclo[3.3.0]octane-3-S-carboxylic acid N-(1-S-carboethoxy-3-(4-fluorophenylpropyl)-S-alanyl-cis-endo-azabicyclo[3.3.0]octane-3-S-carboxylic acid N-(1-S-carboethoxy-3-(4-methoxyphenylpropyl)-S-alanyl-cis-endo-2-azabicyclo[3.3.0]octane-3-S-carboxylic acid N-(1-S-carboethoxy-3-phenylpropyl)-S-lysyl-(2S,3aR,6aS)-octahydrocyclopenta[b]pyrrole-2-carboxylic acid N-(1-S-carboethoxy-3-cyclohexylpropyl)-lysyl-(2S,3a,6aS)-octahydrocyclopenta[b]pyrrole-2-carboxylic acid N-(1-S-carboethoxy-3-phenylpropyl)-O-ethyl-S-tyrosyl-(2S,3aR,6aS)-octahydrocyclopenta[b]pyrrole-2-carboxylic acid N-(1-S-carboethoxy-3-phenylpropyl)-S-alanyl-2-(2S,3aR,6aS)-octahydrocyclopenta[b]pyrrole-2-carboxylic acid N-(1-S-carboethoxy-3-phenylpropyl)-S-alanyl-2-azaspiro[4.5]decane-3-S-carboxylic acid N-(1-S-carboethoxy-3-phenylpropyl)-O-ethyl-2-tyrosylazaspiro-[4.5]decane-3-S-carboxylic acid N-(1-S-carboethoxy-3-phenylpropyl)-S-lysyl-2-azaspiro[4.5]decane-3-S-carboxylic acid N-(1-S-carboethoxy-3-cyclohexylpropyl)-S-alanyl-2-azaspiro[4.5]decane-3-S-carboxylic acid N-(1-S-carboethoxy-3-cyclohexylpropyl)-S-lysyl-2-azaspiro[4.5]decane-3-S-carboxylic acid N-(1-S-carboethoxy-3-phenylpropyl)-S-alanyl-2-azaspiro[4.4]nonane-3-S-carboxylic acid N-(1-S-carboethoxy-3-phenylpropyl)-O-ethyl-S-tyrosyl-2-azaspiro[4.4]nonane-3-S-carboxylic acid N-(1-S-carboethoxy-3-phenylpropyl)-S-lysyl-2-azaspirol[4.4]nonane-3-S-carboxylic acid N-(1-S-carboethoxy-3-cyclohexylpropyl)-S-alanyl-2-azaspiro[4.4]nonane-3-S-carboxylic acid N-(1-S-carboethoxy-3-cyclopentylpropyl)-S-alanyl-2-azaspiro[4.4]nonane-3-S-carboxylic acid N-(1-S-carboethoxy-3-cyclopentylpropyl)-S-lysyl-2-azaspiro[4.4]nonane-3-S-carboxylic acid N-(1-S-carboethoxy-3-phenylpropyl)-S-alanyl-spiro[bicyclo[2.2.1]heptane-2,3'-pyrrolidine]-5'-S-carboxylic acid N-(1-S-carboethoxy-3-phenylpropyl)-O-ethyl-S-tyrosylspiro[bicyclo[2.2.1]heptane-2,3'-pyrrolidine]-5'-S-carboxylic acid N-(1-S-carboethoxy-3-phenylpropyl)-S-lysyl-spiro[bicyclo [2.2.1]heptane-2,3'-pyrrolidine]-5'-S-carboxylic acid N-(1-S-carboethoxy-3-cyclohexylpropyl)-S-alanyl-spiro[bicyclo[2.2.1]heptane 2,3'-pyrrolidine]-5'-S-carboxylic acid N-(1-S-carboethoxy-3-cyclohexylpropyl)-S-lysyl-spirobicyclo[2.2.1]heptane-2,3'-pyrrolidine]-5'-S-carboxylic acid N-(1-S-carboethoxy-3-phenylpropyl)-S-alanyl-spiro-[bicyclo[2.2.2]octane-2,3'-pyrrolidine]-5'-S-carboxylic acid N-(1-S-carboethoxy-3-phenylpropyl)-O-ethyl-tyrosylspiro[bicyclo[2.2.2]octane-2,3'-pyrrolidine]-5'-S-carboxylic acid N-(1-S-carboethoxy-3-phenylpropyl)-S-lysyl-spiro[bicyclo[2.2.2]octane-2,3'-pyrrolidine]-5'-S-carboxylic acid N-(1-S-carboethoxy-3-cyclohexylpropyl)-S-alanyl-spiro-[bicyclo[2.2.2]octane-2,3'-pyrrolidine]-5'-S-carboxylic acid N-(1-S-carboethoxy-3-phenylpropyl)-S-alanyl-2-azatricyclo[4.3.0.1$^{6,9}$]decane-3-S-carboxylic acid N-(1-S-carboethoxy-3-phenylpropyl)-O-ethyl-S-tyrosyl2-azatricyclo[4.3.0.1$^{6,9}$]decane-3-S-carboxylic acid N-(1-S-carboethoxy-3-phenylpropyl)-S-lysyl-2-azatricyclo[4.3.0.1$^{6,9}$]decane-3-S-carboxylic acid N-(1-S-carboethoxy-3-cyclohexylpropyl)-S-alanyl-2azatricyclo[4.3.0.1$^{6,9}$]decane-3-S-carboxylic acid N-(1-S-carboethoxy-3-cyclohexylpropyl)-S-lysyl-2-azatricyclo[4.3.0.1$^{6,9}$]decane-3-S-carboxylic acid N-(1-S-carboethoxy-3-phenylpropyl)-S-alanyl-decahydrocyclohepta[b]pyrrole-2-S-carboxylic acid N-(1-S-carboethoxy-3-phenylpropyl)-O-ethyl-S-tyrosyldecahydrocyclohepta[b]pyrrole-2-S-carboxylic acid N-(1-S-carboethoxy-3-phenylpropyl)-S-lysyl-decahydrocyclohepta[b]pyrrole-2-S-carboxylic acid N-(1-S-carboethoxy-3-cyclohexylpropyl)-S-alanyl-decahydrocyclohepta[b]pyrrole-2-S-carboxylic acid N-(1-S-carboethoxy-3-cyclohexylpropyl)-S-lysyl-decahydrocyclohepta[b]pyrrole-2-S-carboxylic acid N-(1-S-carboethoxy-3-phenylpropyl)-S-alanyl-trans-octahydroisoindole-1-S-carboxylic acid N-(1-S-carboethoxy-3-phenylpropyl)-S-alanyl-cis-octahydroisoindole-1-S-carboxylic acid N-(1-S-carboethoxy-3-cyclohexylpropyl)-S-alanyl-transoctahydroisoindole-1-S-carboxylic acid N-(1-S-carboethoxy-3-cyclohexylpropyl)-S-alanyl-cis-octa-hydroisoindole-1-S-carboxylic acid N-(1-S-carboethoxy-3-phenylpropyl)-S-alanyl-cis-octahydrocyclopenta[c]pyrrole-1-S-carboxylic acid N-(1-S-carboethoxy-3-cyclohexylpropyl)-S-alanyl-cis-octahydrocyclopenta[c]pyrrole-1-S-carboxylic acid benzyl ester N-(1-S-carboethoxy-3-cyclohexylpropyl)-S-lysyl-cis-octahydrocyclopenta[c]pyrrole-1-S-carboxylic acid N-(1-S-carboethoxy-3-phenylpropyl)-S-alanyl-2,3,3a,4,5,7a-hexahydroindole-cis-endo-2-S-carboxylic acid N-(1-S-carboethoxy-3-phenylpropyl)-S-lysyl-2,3,3a,4,5,7a-hexahydroindole-cis-endo-2-S-carboxylic acid N-(1-S-carboethoxy-3-cyclohexylpropyl)-S-lysyl-2-azabicyclo[3.1.0]hexane-3-S-carboxylic acid N-(1-S-carboxy-3-phenylpropyl)-S-lysyl-2-azabicyclo[3.1.0]hexane-cis-endo-3-S-carboxylic acid N-(1-S-carboethoxy-3-cyclopentylpropyl)-S-alanyl-2-azabicyclo[3.1.0]hexane-3-carboxylic acid N-(1-S-carboethoxy-3-phenylpropyl)-S-alanyl-cis-endo-2-azabicyclo[ 3.1.0]hexane-3-S-carboxylic acid N-(1-S-carboethoxy-3-cyclohexylpropyl)-S-alanyl-cis-endo-2-azabicyclo[3.1.0]hexane-3-S-carboxylic acid.

These compounds can be prepared by, for example, the process described in German Patent Application P 3,333,455.2, in which process the tert.-butyl or benzyl esters described in the application are converted into the monocarboxylic acid derivatives in known manner by acid or alkaline hydrolysis or by hydrogenolysis catalyzed by noble metals. The Nε-benzyloxycarbonyl protective group of the lysine derivatives is removed by hydrogenolysis catalyzed by noble metals. The compounds listed above can be readily converted with physiologically tolerated acids or bases (in the case of mono- or dicarboxylic acids) into the corresponding salts (for example hydrochlorides, maleates, fumarates etc.) and be used as salts according to the invention.

The compounds of the formula I are inhibitors of angiotensin converting enzyme (ACE) or intermediates in the preparation of such inhibitors, and they can also be used to control high blood pressure of various etiologies. The compounds of the formula I are disclosed in, for example, U.S. Pat. No. 4,129,571, U.S. Pat. No. 4,374,829, European Patent A-79,522, European Patent A-79,022, European Patent A-49,658, European Patent A-51,301, U.S. Pat. No. 4,454,292, U.S. Pat. No. 4,374,847, European Patent A-72,352, U.S. Pat. No. 4,350,704, European Patent A-50,800, European Patent A-46,953, U.S. Pat. No. 4,344,949 European Patent A-84,164, U.S. Pat. No. 4,470,972, European Patent A-65,301 and European Patent A-52,991.

Also advantageous are orally effective ACE inhibitors such as, for example, ramipril, enalapril, captopril, lisinopril, perindopril, cilazapril, RHC 3659, CGS 13945, CGS 13928C, CGS 14824A, CI-906, SCH 31846, zofenopril, fosenopril, alacepril and others. Orally effective ACE inhibitors are described in, for example, Brunner et al., J. Cardiovasc. Pharmacol. 7 (Suppl. I) (1985) S2-S11.

Preferred ACE inhibitors are those disclosed in European Patent A-79022, of the formula III

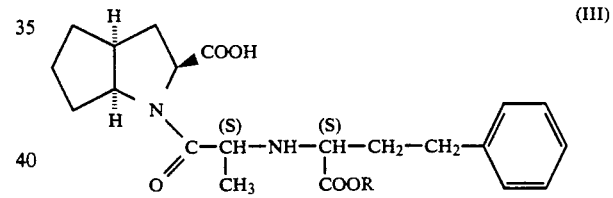

in which R denotes hydrogen, methyl, ethyl or benzyl, in particular the compound of the formula III in which R denotes ethyl (ramipril).

Other preferred ACE inhibitors are those disclosed in European Patent A-84,164, of the formula IV

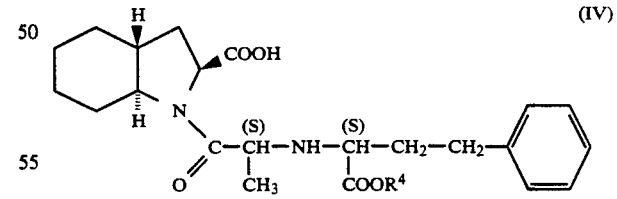

in which $R^4$ denotes hydrogen, $C_1$-$C_4$-alkyl or benzyl, in particular the compound of the formula IV, in which $R^4$ denotes ethyl.

In carrying out the method according to the invention, the angiotensin converting enzyme inhibitors described above can be administered to mammals such as monkeys, dogs, cats, rats, humans etc. The compounds which are suitable for the use according to the invention are advantageously incorporated in pharmaceutical products in customary manner. They can be converted into the customary administration forms, such as capsules, tablets, coated tablets, solutions, ointments and emulsions, as well as into a depot form. The active compound can, where appropriate, also be in microencapsulated form. The products can contain additional, tolerated organic or inorganic substances, for example granulating auxiliaries, adhesives and binders, lubricants, suspending agents, solvents, antibacterial agents, wetting agents and preservatives. Forms for oral and parenteral administration are preferred. The compounds of the formula I can be administered in dosages of 0.1-50 mg per dose once to three times a day.

It is also possible according to the invention to use the ACE inhibitors in combination with substances which influence prostaglandin metabolism. Examples of such substances are stable prostacyclin analogs, inhibitors of thromboxane synthetase, and thromboxane antagonists.

Hence the invention also relates to pharmaceutical compositions containing a) an ACE inhibitor or its physiologically tolerated salt and b) a substance which influences prostaglandin metabolism or its physiologically tolerated salt, and to their use for the treatment of atherosclerosis, of thrombosis and/or of peripheral vessel disease.

The invention furthermore relates quite generally to products containing the substances mentioned above under a) and b), as combination products for concurrent, separate or sequential administration for the treatment of atherosclerosis, of thrombosis and/or of peripheral vessel disease.

An increased aggregability of the blood platelets plays a particularly important part in the development of atherosclerosis. Examples of sequelae are thromboses and peripheral vessel disease; these diseases are the main cause of the increased morbidity and mortality associated with high blood pressure. Blood platelets contain an angiotensin-I-processing system, and their membrane has binding sites with high affinity for angiotensin II. The fact that angiotensin converting enzyme (ACE) is preponderantly located on the luminal cytoplasmic membrane of the endothelial cells points to platelet/endothelium interactions being associated with local angiotensin II production; ACE inhibitors can interfere with this. Furthermore, inhibition of ACE potentiates the action of bradykinin by preventing its breakdown. It is known that bradykinin is a potent stimulator of the release of prostacyclin from endothelial cells; bradykinin is in turn a potent inhibitor of platelet aggregation.

The activity of the compounds of the formula I on platelet aggregation and thus on atherosclerosis, thrombosis and peripheral vessel disease, as well as other disease states associated with increased aggregability of the blood platelets, can be deduced from a variety of test models.

In each of the examples which follow use is made of the results with N-(1-S-carboethoxy-3-phenylpropyl)-S-alanyl-cis-endo-2-azabicyclo[3.3.0]octane-3-S-carboxylic acid (Formula II).

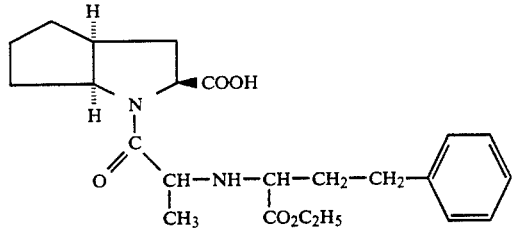

A In vitro results

Platelet-rich rabbit plasma is obtained as stated by Born (Arzneimittel-Forsch. 31, 2012 (1981)). Platelet aggregation is measured by the increase in light passing through a cell which contains this plasma. The platelet count is adjusted to $450,000/mm^3$ by dilution with autologous, platelet-poor plasma. The compound of the formula II has, in concentrations of 0.1-10 μg/ml of plasma, no effect on the aggregation induced by 0.24 mmol/l arachidonic acid, 5 mmol/l ADP or 4 pg/ml collagen. In contrast, the inhibition, brought about by 4 μg/ml $PGI_2$, of aggregation caused by arachidonic acid is increased to 100% by the compound of the formula II in the said dose range.

B. In vivo results

1. Acute study

Conscious rabbits received a single oral dose of 1.0-10.0 mg/kg of the compound of the formula II. After 1 hour, the animals are sacrificed, and platelet-rich plasma is obtained. Platelet aggregation is determined as described under A).

There is found to be a reduction in aggregation in response to the three stimulators described there, in particular in response to arachidonic acid. A potentiation of the $PGI_2$ effect is also observed.

Chronic study

Conscious rabbits received 1 mg/kg/d of the compound of the formula II for 14 days, and then the procedure was continued as described under 1). Pronounced inhibition of the platelet aggregation induced by arachidonic acid and ADP is found in all animals.

The examples which follow indicate the forms for administration to treat atherosclerosis, thrombosis and peripheral vessel disease by the method according to the invention. The compounds of the formula I can be converted into the corresponding forms for administration in analogy to the examples.

EXAMPLE 1

Preparation of the agent used according to the invention for oral administration in the treatment of atherosclerosis, of thrombosis and of peripheral vessel disease.

1000 tablets each containing 10 mg of 1-N-(1-S-carboethoxy-3-phenylpropyl) -S-alanyl-1S,3S,5S-2-azabicyclo-[3.3.0]octane-3-carboxylic acid are prepared with the following auxiliaries:

| | |
|---|---|
| N-(1-S-carboethoxy-3-phenylpropyl)-S-alanyl-1S,3S,5S-2-azabicyclo[3.3.0]octane-3-carboxylic acid | 10 g |
| Corn starch | 140 g |
| Gelatine | 7.5 g |
| Microcrystalline cellulose | 2.5 g |

| | |
|---|---|
| -continued | |
| Magnesium stearate | 2.5 g |

N-(1-S-carbethoxy-3-phenylpropyl)-S-alanyl-1S,3S,5S-2-azabicyclo[3.3.0]octane-3-carboxylic acid and corn starch are mixed with an aqueous gelatine solution. The mixture is dried and milled to granules. Microcrystalline cellulose and magnesium stearate are mixed with the granules. The resulting granules are compressed to form 1000 tablets, each tablet containing 10 mg of the ACE inhibitor.

These tablets can be used for the treatment of atherosclerosis, of thrombosis and/or of peripheral vessel disease.

EXAMPLE 2

1000 tablets each containing 10 mg of N-(1-S-carbethoxy-3-phenylpropyl)-S-alanyl-(2S,3aR,7aS)-octahydroindole-2-carboxylic acid hydrochloride are prepared in analogy to Example 1.

EXAMPLE 3

Gelatine capsules each containing 10 mg of N-(1-S-carboethoxy-3-phenylpropyl)-S-alanyl-1S,3S,5S-2-azabicyclo[3.3.0]octane-3-carboxylic acid are filled with the following mixture:

| | |
|---|---|
| N-(1-S-carboethoxy-3-phenylpropyl)-S-alanyl-1S,3S,5S-2-azabicyclo[3.3.0]octane-3-carboxylic acid | 10 mg |
| Magnesium stearate | 1 mg |
| Lactose | 214 mg |

These capsules can be used for the treatment of atherosclerosis, of thrombosis and/or of peripheral vessel disease.

EXAMPLE 4

The preparation of an injection solution for the treatment of atherosclerosis, of thrombosis and/or of peripheral vessel disease is described below:

| | |
|---|---|
| N-(1-S-carboxy-3-phenylpropyl)-S-alanyl-1S,3S,5S-2-azabicyclo[3.3.0]octane-3-carboxylic acid | 250 mg |
| Methylparaben | 5 g |
| Propylparaben | 1 g |
| Sodium chloride | 25 g |
| Water for injections | 5 l |

N-(1-S-carboxy-3-phenylpropyl)-S-alanyl-1S,3S,5S-2-azabicyclo[3.3.0]octane-3-carboxylic acid, the preservatives and sodium chloride are dissolved in 3 l of water for injections, and the solution is made up to 5 l with water for injections. The solution is filtered sterile, and dispensed aseptically into presterilized bottles, which are closed with sterilized rubber caps. Each bottle contains 5 ml of solution.

EXAMPLE 5

Tablets which can be used for the treatment of atherosclerosis, of thrombosis and/or of peripheral vessel disease are prepared as described in Example 1, with the exception that in place of N-(1-S-carboethoxy-3-phenylpropyl)-S-alanyl-1S,3S,5S-2-azabicyclo[3.3.0]-octane-3S-carboxylic acid N-(1-S-carboxy-3-phenylpropyl)-S-alanyl-1S,3S,5S-2-azabicyclo[3.3.0]octane-3-carboxylic acid or N-(1-S-carboxy-3-phenylpropyl)-S-alanyl-2S,3aR,-7aS-octahydroindole-2-carboxylic acid or N-(1-S-carboethoxy-3-phenylpropyl)-S-alanyl-cis-2,3,3a,4,5,7a-hexahydro[1H]indole-2-S-endo-carboxylic acid or N-(1-S-carboxy-3-phenylpropyl)-S-alanyl-cis-2,3,3a,4,5,7a-hexahydro[1H]indole-2S-endo-carboxylic acid or N-(1-S-carboxy-3-phenylpropyl)-S-lysyl-1S,3S,5S-2-azabicyclo[3.3.0]octane-3-carboxylic acid or N-(1-S-carboethoxy-3-cyclohexylpropyl)-S-alanyl-1S,3S,5S-2-azabicyclo[3.3.0]octane-3-carboxylic acid or N-(1-S-carboxy-3-cyclohexylpropyl)-S-lysyl-1S,3S,5S-2-azabicyclo[3.3.0]octane-3-carboxylic acid are used.

EXAMPLE 6

An injection solution is prepared in analogy to the procedure described in Example 4, with the exception that in place of N-(1-S-carboethoxy-3-phenylpropyl)-S-alanyl- 1S,3S,5S-2-azabicyclo[3.3.0]octane-3-carboxylic acid N-(1-S-carboxy-3-phenylpropyl)-S-alanyl-1S,3S,5S-2-azabicyclo[3.3.0]octane-3-carboxylic acid or N-(1-S-carboethoxy-3-phenylpropyl)-S-alanyl-2S,3aR,7aS-octahydroindole-2-carboxylic acid hydrochloride or N-(1-S-carboxy-3-phenylpropyl)-S-alanyl-2S,3aR,-7aS-octahydroindole-2-carboxylic acid or N-(1-S-carboethoxy-3-cyclohexylpropyl)-S-alanyl-cis-2,3,3a,4,5,7a-hexahydro[1H]indole-2-S-endo-carboxylic acid or N-(1-S-carboxy-3-phenylpropyl)-S-alanyl-cis-2,3,3a,4,5,7a-hexahydro[1H]indole-2-S-endo-carboxylic acid or N-(1-carboxy-3-phenylpropyl)-S-lysyl-1S,3S,5S-2-azabicyclo[3.3.0]octane-3-carboxylic acid or N-(1-S-carboethoxy-3-cyclohexyl)-S-alanyl-1S,3S,5S-2-azabicyclo[3.3.0]octane-3-carboxylic acid or N-(1-S-carboxy-3-cyclohexylpropyl)-S-lysyl-1S,3S,5S-2-azabicyclo[3.3.0]octane-3-carboxylic acid are used.

I claim:

1. A method for the treatment of a circulatory and/or circulatory related disease in a mammal comprising the step of administering to a mammal in recognized need of said treatment, for the purpose of suppressing platelet aggregation, an angiotensin converting enzyme inhibitor of formula I or its physiologically tolerated salt in an amount effective to suppress platelet aggregation;

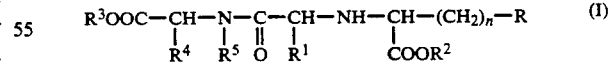

in which n is 1 or 2,

R denotes $(C_1-C_6)$-alkyl or $(C_6-C_{12})$-aryl;

$R^1$ denotes hydrogen or $(C_1-C_6)$-alkyl which can optionally be substituted by amino;

$R^2$ and $R^3$ are identical or different and denote hydrogen, $(C_1-C_6)$-alkyl, $(C_2-C_6)$-alkenyl or $(C_6-C_{12})$-aryl-$(C_1-C_4)$-alkyl; and $R^4$ and $R^5$ form, together with the atoms carrying them, a heterocyclic ring system selected from tetrahydroisquinoline, decahydroisoquinoline, octahydroindole, and octahydrocyclopenta[b]pyrrole.

2. The method of claim 1 wherein $R^2$ and $R^3$ are hydrogen.

3. The method of claim 1 wherein $R^2$ and $R^3$ are ethyl.

4. The method of claim 1 wherein said angiotensin converting enzyme inhibitor of formula I is [S,S,S,S,S]-N-(1-carboethoxy-3-phenylpropyl)-alanyl-octahydroindole-2-carboxylic acid, N-[1-(S)-carboethoxy-3-phenylpropyl)-(S)-alanyl]-2S,3aR,7aS-octahydroindole-2-carboxylic acid [S,S,S,S,S]-N-[(1-carboethoxy-3-phenylpropyl)-alanyl]-decahydroisoquinoline-3-carboxylic acid, N-(1-S-carboethoxy-3-phenylpropyl)-S-alanyl-cis-endo-2-azabicyclo[3.1.0 hexane-3-S-carboxylic acid, or N-(1-S-carboethoxy-3-phenylpropyl)-S-alanyl-cis-endo-2,3,3a,4,5,7a-)-hexahydroindole-2-S-carboxylic acid.

5. The method of claim 1 wherein said angiotensin converting enzyme inhibitor of formula I is a physiologically tolerated salt of [S,S,S,S,S]-N-(1-carboethoxy-3-phenylpropyl)-alanyl-octahydroindole-2-carboxylic acid, N-[2-(S)-carboethoxy-3-phenylpropyl)-(S)-alanyl]-2S,3aR,7aS-octahydroindole-2-carboxylic acid [S,S,S,S,S]-N-[(1-carboethoxy-3-phenylpropyl)-alanyl]-decahydroisoquinoline-3-carboxylic acid, N-(1-S-carboethoxy-3-phenylpropyl)-S-alanyl-cis-endo-2-azabicyclo[3.1.0]hexane-3-S-carboxylic acid or N-(1-S-carboethoxy-3-phenylpropyl)-S-alanyl-cis-endo-2,3,3a,4,5,7a-hexahydroindole-2-S-carboxylic acid.

6. The method of claim 1 wherein said angiotensin converting enzyme inhibitor of formula I is N-(1-S-carboethoxy-3-phenylpropyl)-S-alanyl-cis-endo-2-azabicyclo[3.3.0]octane-3-S-carboxylic acid or a physiologically tolerated salt thereof.

* * * * *

UNITED STATES PATENT AND TRADEMARK OFFICE
CERTIFICATE OF CORRECTION

PATENT NO. : 5,231,080
DATED : July 27, 1993
INVENTOR(S) : Bernward Scholkens

It is certified that error appears in the above-indentified patent and that said Letters Patent is hereby corrected as shown below:

Claim 5, column 16, line 5, change
"N-[2-(S)-carboethoxy-3-phenylpropyl)-(S)-"
to --N-[1-(S)-carboethoxy-3-phenylpropyl)-(S)- --.

Signed and Sealed this

Twentieth Day of September, 1994

Attest:

BRUCE LEHMAN

*Attesting Officer*    *Commissioner of Patents and Trademarks*